United States Patent [19]
Lorant

[11] Patent Number: 5,952,395
[45] Date of Patent: Sep. 14, 1999

[54] GELLED ULTRAFINE OIL-IN-WATER EMULSION STABILIZED WITH A CROSSLINKED POLY(2-ACRYLAMIDO-2-METHYLPROPANESULFONIC ACID) POLYMER NEUTRALIZED TO AT LEAST 90% PROCESS OF PREPARATION AND APPLICATIONS

[75] Inventor: Raluca Lorant, Thiais, France

[73] Assignee: L'Oreal, France

[21] Appl. No.: 08/885,592

[22] Filed: Jun. 30, 1997

[30] Foreign Application Priority Data

Jun. 28, 1996 [FR] France .................................. 96 08111

[51] Int. Cl.$^6$ .............................. A61K 9/10; A61K 47/32
[52] U.S. Cl. ...................................... 514/772.4; 424/70.11
[58] Field of Search ............................... 514/772.6, 772.4

[56] References Cited

U.S. PATENT DOCUMENTS

| | | | |
|---|---|---|---|
| 5,114,706 | 5/1992 | Duvel | 424/70 |
| 5,534,265 | 7/1996 | Fowler et al. | 424/70.1 |

FOREIGN PATENT DOCUMENTS 40 10 393   10/1991   Germany .

*Primary Examiner*—Peter F. Kulkosky
*Attorney, Agent, or Firm*—Finnegan, Henderson, Farabow, Garrett & Dunner, L.L.P.

[57] ABSTRACT

The present invention relates to cosmetic or dermatological compositions in the form of an ultrafine oil-in-water emulsion wherein the mean size of the particles or globules which form the fatty phase ranges from 50 nm to 1000 nm, and wherein the composition also contains at least one crosslinked poly(2-acrylamido-2-methylpropanesulphonic acid) polymer neutralized to at least 90%. These compositions may be obtained according to an emulsifying technique using phase inversion. These compositions are stable in all viscosity ranges with a large variety of possible emulsifiers and whatever oils are employed. They can contain a large variety of cosmetic active substances and adjuvants without disturbing their stability and they can be employed in many cosmetic and dermatological applications and adapted to all types of skin.

42 Claims, No Drawings

GELLED ULTRAFINE OIL-IN-WATER EMULSION STABILIZED WITH A CROSSLINKED POLY(2-ACRYLAMIDO-2-METHYLPROPANESULFONIC ACID) POLYMER NEUTRALIZED TO AT LEAST 90% PROCESS OF PREPARATION AND APPLICATIONS

The present invention relates to a cosmetic or dermatological composition in the form of an ultrafine oil-in-water emulsion capable of being obtained by phase inversion, gelled and stabilized with at least one crosslinked poly(2-acrylamido-2-methylpropanesulphonic acid) polymer neutralized to at least 90%.

For various reasons linked in particular with better comfort in use, such as mildness, softness and others, current cosmetic or dermatological compositions are in most cases presented in the form of an emulsion of the oil-in-water type, i.e., a substrate consisting of an aqueous dispersing continuous phase and an oily dispersed noncontinuous phase, or an emulsion of the water-in-oil type, i.e., a substrate consisting of a fatty dispersing continuous phase and an aqueous dispersed noncontinuous phase. Oil-in-water emulsions are in greatest demand in the field of cosmetics because, when applied, they make the skin feel softer, less greasy and lighter than do water-in-oil emulsion systems.

One of the fundamental parameters affecting the stability of oil-in-water emulsions, which will be denoted by O/W, is the size of the dispersed oil droplets, which is in relation with the surface tension between the noncontinuous phase and the continuous phase. The smaller the size of the oil droplets, the more the surface tension decreases and the more the stability of the emulsion increases.

Oil-in-water emulsions are generally stabilized with emulsifying surfactants of the oil-in-water type which, because of their amphiphilic structure, move to the oil/water interface and thus stabilize the dispersed droplets. In most cases the increase in emulsifying agent allows the stability of the emulsion to be improved. Their presence in high concentrations gives rise to anticosmetic effects such as a rough feel, sticky or tacky feel and to problems of harmlessness to the skin, the eyes and the scalp.

To solve the problems of stability of conventional O/W emulsions it has been proposed to produce so-called "ultrafine" specific O/W emulsions in which the mean size of the globules forming the fatty phase is within well-determined limits, namely between 50 and 1000 nm, the ultrafine emulsions of O/W type being themselves obtained according to an emulsifying technique using phase inversion.

This technique is, in its principle, well known to a person skilled in the art and is described especially in the articles "Phase Inversion Emulsification", by Th. Forster et al., published in Cosmetics & Toiletries, vol. 106, December 1991, pp. 49–52 and "Application of the phase-inversion-temperature method to the emulsification of cosmetics" by T. Mitsui et al., published in American Cosmetics and Perfumery, vol. 87, December 1972. Its principle is thus the following: an emulsion is prepared (introduction of water into the oil) at a temperature which must be higher than the phase inversion temperature (PIT) of the system, that is the temperature at which the equilibrium between the hydrophilic and lipophilic properties of the emulsifier(s) used is reached; at an elevated temperature (>PIT) the emulsion is of the water-in-oil type and, as it cools, at the phase inversion temperature this emulsion is inverted to become an emulsion of, this time, oil-in-water type, and does so by having previously passed through a microemulsion state.

These emulsions are extremely fluid. They have a bluish appearance and are translucent. Emulsions of these types are fragile and still pose a number of stability problems. Phenomena of creaming, of dephasing after several freezing cycles, of coiling and of deposits which are difficult to identify are also observed. Furthermore, the production of ultrafine emulsions makes it necessary to employ very specific oils and emulsifying agents in specified conditions, and the addition of certain cosmetic active substances and ingredients is tricky and often results in destabilization of the emulsion. Finally, the extreme fluidity of these emulsions limits their use to a very restricted viscosity range and to very specific cosmetic or dermatological fields and is not suitable for all skins.

In theory, gelling of this type of emulsion should make it possible to improve its stability and to widen the viscosity range so as to make it possible to employ it in any cosmetic and dermatological fields and to diversify its textures in order to adapt them to all types of skin.

Unfortunately, the gelling agents commonly employed in cosmetics are, for the most part, poor in performance and some are incompatible with this type of emulsion. In general, conventional gelling agents do not make it possible to thicken homogeneously the emulsions obtained by phase inversion and to stabilize them in different viscosity ranges.

In particular, the acrylate/acrylic acid copolymers such as the product SALCARE SC 97 from Allied Colloids destabilize the emulsions obtained by phase inversion and acrylamide/2-acrylamido-2-methylpropanesulphonic acid copolymers such as the SEPIGEL products from Seppic give rise to heterogeneous emulsions and creaming phenomena. Cellulose derivatives and polyacrylics of the CARBOPOL type from Goodrich impart a sticky feel and do not improve the emulsions obtained by phase inversion which present stability problems.

The inventor has surprisingly discovered a new class of thickening or gelling polymers which make it possible to produce emulsions obtained by phase inversion, which are stable in all the viscosity ranges, for example ranging from 10 to 30,000 cP, with a wide variety of possible emulsifiers and regardless of the oils employed. This new class makes it possible to solve all the problems which are specific to this type of emulsion and which have been referred to above.

The inventor has also discovered that this new class of thickening or gelling polymers makes it possible to produce ultrafine emulsions which can contain a wide range of cosmetic active substances and adjuvants without disturbing their stability.

When employed in a low proportion, the gelling agents of the invention, which will be defined later, do not modify the extremely fluid viscosity of the emulsions obtained by phase inversion in which they are present, but make these emulsions film-forming, milder and comfortable in application.

By gradually increasing the proportion of gelling agent in accordance with the invention it is possible to obtain more or less fluid, cool and comfortable smooth milk or else more or less thick, smooth, mild creams which are rich and light at the same time.

This diversification of the textures which is thus obtained using the gelling agents of the invention makes it possible to increase the number of the fields of utilization of the emulsions obtained by phase inversion and to enable them to be adapted to all types of skin.

When compared with the conventional oil/water emulsions, ultrafine oil/water emulsions of the invention which are gelled with the specific polymers which will be defined later exhibit, besides their greater stability, substantially improved cosmetic properties such as mildness, coolness and comfort in application, as well as an original sensation of melting and of slipperiness.

The present invention relates to a cosmetic or a dermatological composition in the form of an ultrafine oil-in-water emulsion in which the mean size of the globules which form the oily phase ranges from 50 nm to 1000 nm (nanometres), characterized in that it contains at least one crosslinked poly(2-acrylamido-2-methylpropanesulphonic acid) polymer neutralized to at least 90%.

The oil-in-water emulsions of the invention may be obtained according to the emulsifying technique using phase inversion.

The crosslinked and virtually or completely neutralized poly(2-acrylamido-2-methylpropanesulphonic acid) polymers in accordance with the invention are water-soluble or swellable in water. They are in general characterized in that they comprise, distributed randomly:

(a) from 90 to 99.9% by weight, relative to the weight of said at least one crosslinked polymer, of units of following formula (1):

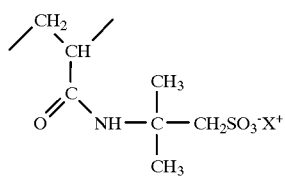
(1)

in which $X^+$ denotes a cation or a mixture of cations, it being possible for at the most 10 mol % of the cations $X^+$ to be protons $H^+$; and (b) from 0.01 to 10% by weight, relative to the weight of said at least one crosslinked polymer, of crosslinking units originating from at least one monomer containing at least two olefinic double bonds.

The polymers of the invention preferably contain a number of units of formula (1) in a quantity which is sufficiently high to obtain polymer particles whose hydrodynamic volume in solution in water has a radius ranging from 10 to 500 nm and whose distribution is homogeneous and unimodal.

The more particularly preferred polymers according to the invention comprise from 98 to 99.5% by weight of units of formula (1) and from 0.2 to 2% by weight of crosslinking units.

$X^+$ denotes a cation or a mixture of cations which are chosen in particular from a proton, an alkali metal cation, a cation equivalent to that of an alkaline-earth metal or the ammonium ion.

More particularly, 90 to 100 mol % of the cations are $NH_4^+$ cations and 0 to 10 mol % are protons ($H^+$).

The crosslinking monomers containing at least two olefinic double bonds are selected, for example, from dipropylene glycol diallyl ether, polyglycol diallyl ethers, triethylene glycol divinyl ether, hydroquinone diallyl ether, tetraallyloxyethanoyl or other allyl or vinyl ethers polyfunctional alcohols, tetraethylene glycol diacrylate, triallylamine, trimethylolpropane diallyl ether, methylenebisacrylamide or divinylbenzene.

The crosslinking monomers containing at least two olefinic double bonds are more particularly selected from those corresponding to the following formula (2):

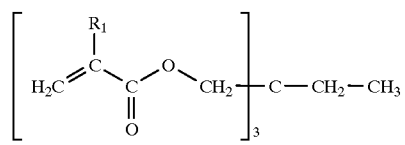
(2)

in which $R_1$ denotes a hydrogen atom or a $C_1$–$C_4$ alkyl. The crosslinking monomers containing at least two olefinic double bonds are more particularly methyl (trimethylolpropane triacrylate).

The polymerization reaction of the polymers of the invention produces not only linear chains but also branched or crosslinked polymer molecules. These molecules can be characterized especially by their Theological behavior in water, and more particularly by dynamic scattering of light.

In the case of the characterization of the molecules by dynamic scattering of light the distribution of the hydrodynamic volume of the polymer structures is measured. Macromolecules dissolved in water are flexible and surrounded by a solvation shell made up of water molecules. With charged polymers such as those of the invention the size of the molecules depends on the quantity of salt in the water. In polar solvents the uniform charge along the main chain of the polymer produces a large expansion of the polymer chain. The fact of increasing the quantity of salt increases the quantity of electrolyte in the solvent and screens the uniform charges of the polymer. In addition to the molecules carried in the solvation shell, the solvent molecules are bound in the cavities of the polymer. In this case the solvent molecules form part of the macromolecules in solution and travel at the same average speed. The hydrodynamic volume thus describes the linear dimension of the macromolecule and of these solvating molecules.

The hydrodynamic volume $v_h$ is determined by the following formula:

$$v_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d the mass in grams of the solvent which is associated with 1 gram of undissolved macromolecule.

If the hydrodynamic particle is spherical, then it is easy to calculate the hydrodynamic radius from the hydrodynamic volume using the formula:

$$V_h = 4\pi R^3/3$$

with R denoting the dynamic radius.

The cases in which the hydrodynamic particles are perfect spheres are extremely rare. Most of the synthetic polymers involve compacted structures or ellipsoids of high eccentricity. In this case the determination of the radius is performed on a sphere which is equivalent, from a viewpoint of friction, to the form of the particle being considered.

As a general rule, work is done on molecular weight distributions and hence on distributions of hydrodynamic radius and volume. In the case of polydisperse systems the distribution of the diffusion coefficients must be calculated. From this distribution are deduced the results relating to the radial distribution and to the distribution of hydrodynamic volumes.

The hydrodynamic volumes of the polymers of the invention are, in particular, determined by dynamic light scattering from diffusion coefficients D according to Stokes-Einstein, of formula: $D=kT/6\pi\eta R$ where k is Boltzmann's constant, T the absolute temperature in degrees Kelvin, $\eta$ is the viscosity of the solvent (water) and R is the hydrodynamic radius.

These diffusion coefficients D are measured according to the method for characterizing a mixture of polymers by laser scattering, described in the following references:

(1) Pecora, R.; Dynamic Light Scattering; Plenum Press, New York, 1976;

(2) Chu, B.; Dynamic Light Scattering; Academic Press, New York, 1994;

(3) Schmitz, K. S.; Introduction to Dynamic Light Scattering; Academic Press, New York, 1990;

(4) Provincher S. W.; Comp. Phys., 27,213,1982;

(5) Provincher S. W.; Comp. Phys., 27,229, 1982;

(6) ALV Laservertriebgesellschaft mbH, Robert Bosch Str. 47, D-63225 Langen, Germany;

(7) ELS-Reinheimer Strasse 11, D-64846 Gross-Zimmern, Germany; and (8) Chi Wu et al., Macromolecules, 1995, 28, 4914–4919.

The polymers which are particularly preferred are those exhibiting a viscosity, measured with a Brookfield viscometer, spindle 4, at a speed of rotation of 100 revolutions/minute in a water solution at a concentration of 2% and at 25° C., which is higher than or equal to 1000 cP and more preferably ranging from 5000 to 40,000 cP and most preferably from 6500 to 35,000 cP.

The at least on crosslinked poly(2-acrylamido-2-methylpropanesulphonic acid) polymer of the invention can be obtained according to the process of preparation including the following stages:

(a) the 2-acrylamido-2-methylpropanesulphonic acid monomer in free form is dispersed or dissolved in a solution of tert-butanol or water and tert-butanol;

(b) the monomer solution or dispersion obtained in (a) is neutralized with one or several inorganic or organic bases, preferably aqueous ammonia ($NH_3$) in a quantity which makes it possible to obtain a degree of neutralization of the sulphonic acid functional groups of the polymer ranging from 90 to 100%;

(c) the crosslinking monomer(s) is(are) added to the solution or dispersion obtained in (b);

(d) a conventional radical polymerization is performed in the presence of free-radical initiators at a temperature ranging from 10 to 150° C., the polymer precipitating in the solution or dispersion based on tert-butanol.

The nature of the oily or fatty phase forming part of the composition of the emulsions according to the invention is not critical and it can thus comprise any of the compounds which are already generally known as suitable for the manufacture of emulsions of oil-in-water type. In particular these compounds may be selected, alone or as mixtures, from the various fatty substances, oils of vegetable, animal or mineral origin, natural or synthetic waxes and the like.

Among the oils which can form part of the composition of the fatty phase there may be mentioned in particular:

mineral oils such as liquid paraffin and liquid petrolatum;

oils of animal origin such as perhydrosqualene;

oils of vegetable origin such as sweet almond oil, avocado oil, castor oil, olive oil, jojoba oil, sesame oil, groundnut oil, grape seed oil, rape oil, copra oil, hazelnut oil, shea butter, palm oil, apricot kernel oil, calophyllum oil, rice husk oil, corn germ oil, wheat germ oil, soya oil, sunflower oil, evening primrose oil, safflower oil, passionflower oil and rye oil; and synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and the esters derived from lanolic acid such as isopropyl lanolate and isocetyl lanolate, isoparaffins and poly-α-olefins.

As other oils which can be employed in the emulsions according to the invention it is also possible to mention benzoates of $C_{12}$–$C_{15}$ fatty alcohols (FINSOLV TN from Finetex), fatty alcohols such as lauryl, cetyl, myristyl, stearyl, palmityl and oleyl alcohol and 2-octyldodecanol, acetylglycerides, octanoates and decanoates of alcohols and of polyalcohols such as those of glycol and of glycerol, resinoleates of alcohols and of polyalcohols such as cetyl, fatty acid triglycerides such as caprylic/capric triglycerides, triglycerides of $C_{10}$–$C_{18}$ saturated fatty acids, fluorinated and perfluorinated oils, lanolin, hydrogenated lanolin, acetylated lanolin and, finally, volatile or nonvolatile silicone oils like polymethylsiloxanes, polymethylphenylpolysiloxanes, fluorinated silicones and polysiloxanes modified with fatty alcohols or polyoxyalkylenes.

According to an essential characteristic of the compositions in accordance with the present invention, the mean size of the liquid particles (or globules) of fatty phase within the dispersing aqueous phase must be included within quite specific limits, namely from 50 nm to 1000 nm. This mean size is preferably from 70 nm to 350 nm and more preferably from 70 to 300 nm.

The compositions according to the invention are usually characterized by a very narrow polydispersity. As a general rule, 90% of the particles of the ultrafine oil-in-water emulsion according to the invention have a size of from 100 to 300 nm. The difference in size between the largest and the smallest particles is generally from 20 to 400 nm and preferably from 30 to 200 nm, whereas in conventional emulsions (other than PIT emulsions or microemulsions) the difference in size between the largest and the smallest particles is generally greater than 1000 nm.

Conventionally, the dispersing aqueous phase may consist of water or a mixture of water and polyhydric alcohol(s) like, for example, glycerol, propylene glycol and sorbitol or else a mixture of water and of water-soluble lower alcohol(s) such as ethanol, isopropanol or butanol (hydroalcoholic solution) and it may, of course, additionally contain water-soluble conventional cosmetic adjuvants.

Among the conventional cosmetic adjuvants which may be present in the aqueous phase or in the fatty phase of the emulsions in accordance with the invention (according to their water- and/or liposoluble nature) there may be mentioned in particular ionic or nonionic thickeners, softeners, antioxidants, opacifiers, stabilizers, emollients, insect repellents, hydrating agents, vitamins, perfumes, preserving agents, fillers, sequestrants, dyes or any other ingredient usually employed in the field of sun care products.

A person skilled in the art will, of course, take care to choose the optional compound(s) to be added to the composition according to the invention in such a way that the advantageous properties intrinsically linked with the composition in accordance with the invention are not, or substantially are not, damaged by the envisaged addition.

The emulsions in accordance with the invention additionally generally contain specific surfactants or emulsifiers the use of which has been made necessary for preparing and obtaining the ultrafine emulsion. This point will be detailed later. They may additionally contain specific coemulsifiers the purpose of which is, when the emulsion is being prepared, to reduce substantially the quantity of surface-active agents needed to produce the emulsion.

The emulsifiers which can be employed in the present invention are preferably selected from nonionic compounds of a lipophilic residue selected, for example, from $C_6$–$C_{30}$ alkyl or acyl functional groups, and of a hydrophilic residue selected, for example, from glycol groups, glucose and polyol ethers. Their HLB can range from 9 to 18 and more preferably from 9.5 to 11.5.

The HLB (hydrophilic-lipophilic balance) of an emulsifier is calculated according to the following formula:

$$HLB = \frac{100 - L}{5}$$

in which L denotes the percentage by weight of the lipophilic group (that is of the $C_8$–$C_{28}$ alkyl or acyl group) in relation to the weight of the entire molecule.

As nonionic emulsifiers which are preferably employed in the present invention there may be mentioned in particular the products of addition of ethylene oxide to fatty alcohols containing 6 to 30 carbon atoms or to partial esters of polyols containing 3 to 16 carbon atoms and of fatty acids containing 14 to 22 carbon atoms. The products of addition of ethylene oxide to fatty alcohols are available commercially. The products of addition of ethylene oxide to partial esters of polyols and of fatty acids can be easily obtained by ethoxylation of partial fatty acid esters of glycerol or of fatty acid mono- or diesters of sorbitol.

An emulsifier corresponding to the formula (IV):

$$R^4\text{—}(O\text{—}CH_2\text{—}CH_2)_n\text{—}OH \quad (IV)$$

in which $R^4$ denotes a branched or linear, saturated or unsaturated hydrocarbon residue containing from 8 to 28 carbon atoms and n denotes a number ranging from 8 to 50, preferably from 8 to 30, will preferably be employed; it is also possible to employ a product of addition of 4 to 20 moles of ethylene oxide to one or several partial esters of glycerol. Partial esters of glycerol are intended to mean, for example, mixtures of mono-, di- and triglycerides of $C_{10}$–$C_{20}$ fatty acids, obtained by esterification of one mole of glycerol with 1 or 2 moles of a $C_{10}$–$C_{20}$ fatty acid. The emulsifier employed will be preferably the product of condensation of behenyl alcohol and of 9 ethylene oxides or oxyethylenated cetyl alcohols and/or stearyl alcohols containing from 12 to 15 moles of ethylene oxide.

In addition the emulsions according to the invention may furthermore include a coemulsifier which will be preferably selected from $C_{16}$–$C_{22}$ fatty alcohols or the partial esters of $C_3$–$C_6$ polyols with $C_{14}$–$C_{22}$ fatty acids. More preferably the use of glycerol $C_{14}$–$C_{22}$ fatty esters is chosen.

The oil-in-water emulsions in accordance with the invention have preferably the following compositions:

(I) aqueous phase: from 50 to 95% by weight, more preferably from 70 to 90% by weight, relative to the whole formulation, (ii) oily phase: from 0.5 to 50% by weight, more preferably from 10 to 30% by weight, relative to the whole formulation, (iii) crosslinked and practically or completely neutralized poly(2-acrylamido-2-methylpropanesulphonic acid) polymers: from 0.1 to 10% by weight, more preferably from 0.1 to 5% by weight, relative to the whole formulation, (iv) (co)emulsifier(s): from 0.5 to 30% by weight, more preferably from 2 to 10% by weight, relative to the whole formulation.

Another subject-matter of the invention is a process for the preparation of these emulsions.

The emulsions according to the invention can be obtained by a phase inversion process characterized in that the following are mixed:

(a) at least one cosmetic oil, (b) at least one emulsifier and optionally a coemulsifier, (c) water, and optionally (d) adjuvants which are stable at the phase inversion temperature, in order to obtain a conventional emulsion and in that this emulsion is then heated to a temperature situated within or above the phase inversion region or that the emulsion is prepared at such a temperature and in that in a second step the emulsion is then cooled to a temperature lower than the phase inversion region; the emulsion obtained is next gelled by adding a crosslinked and practically or completely neutralized poly(2-acrylamido-2-methylpropanesulphonic acid) polymer as defined above.

The phase inversion temperature region is established for a given composition by measuring the conductivity of a sample of the composition which is heated. When the phase inversion region is reached the conductivity of the emulsion increases very rapidly: in the phase inversion region an increase in the conductivity of approximately 50 microsiemens per centimeter can be observed over a temperature range of 5 to 15° C., whereas it will be only approximately 5 microsiemens per centimeter over an equivalent temperature range outside the phase inversion region.

The compositions of the invention can also be employed as a care or hygiene product such as creams for protection, treatment or care for the face, for the hands or for the body, body creams for protection or care of the skin, of the scalp or of the mucosae or for cleaning the skin.

The compositions according to the invention can be employed as hair-care products. The compositions of the invention can also be employed as an antisun product. The compositions can additionally be products for make-up.

Another subject-matter of the invention is a process for nontherapeutic cosmetic treatment of the skin, of the scalp, of hair, of eyelashes, of eyebrows, of nails or of the mucosae, characterized in that a composition as defined above is applied to the substrate according to the usual technique of use of this composition. For example, such treatment may involve application of creams or milks to the skin, the scalp or the mucosae. The type of treatment is a function of the active substance(s) present in the composition.

Another subject-matter of the invention is a use of the above composition for preparing a salve or an ointment intended for therapeutically treating the face or the human body, including the hands, especially for treating acne and blackheads in fatty skins.

Another subject-matter of the invention is a use of a polymer as defined above for gelling or thickening a cosmetic or dermatological composition in the form of oil-in-water emulsion in which the mean size of the globules which form the oily phase is from 70 nm to 1000 nm.

Another subject-matter of the invention is a use of a polymer as defined above for stabilizing a cosmetic or dermatological composition in the form of oil-in-water emulsion in which the mean size of the globules which form the oily phase is from 70 nm to 1000 nm.

The following examples illustrate the invention without any limitation being implied.

EXAMPLE OF PREPARATION A

Into a 5-liter round bottom flask fitted with a stirrer, a reflux condenser, a thermometer and a conduit device for nitrogen and for aqueous ammonia were introduced 2006.2 g of tert-butanol and then 340.0 g of 2-acrylamido-2-methylpropanesulphonic acid, which was dispersed in the solution with energetic stirring. After 30 minutes aqueous ammonia was added via the upper conduit of the round bottom flask and the reaction mixture was kept for 30 minutes at ambient temperature until a pH of the order of 6–6.5 was obtained. 32.0 g of a solution of trimethylolpropane triacrylate at a concentration of 25% in tert-butanol were introduced next and heating to 60° C. was applied while the reaction mixture was simultaneously made inert by introduction of nitrogen into the flask. Once this temperature was reached, dilauroyl peroxide was added. The reaction commenced immediately, which was reflected in a rise in temperature and a precipitation of the polymerizate. 15 minutes after the polymerization began a stream of nitrogen was introduced. 30 minutes after the addition of the initiator the temperature of the reaction mixture reached a maximum of 65–70° C. 30 minutes after having reached this temperature the mixture was heated to reflux and kept in these conditions for 2 hours. A thick paste was seen to form during the reaction.

The product obtained was cooled to ambient temperature and filtered. The paste recovered was next dried under vacuum at 60–70° C. for 24 hours. 391 g of crosslinked and neutralized poly(2-acrylamido-2-methylpropanesulphonic acid) were obtained, which had a viscosity, measured with a Brookfield viscometer, spindle 4, at a speed of rotation of 100 revolutions/minute in a water solution at a concentration of 2% and at 25° C., ranging from 15 000 cP to 35,000 cP. The viscosity of the polymer may be chosen and controlled by conventional means as a function of the cosmetic application envisaged.

The hydrodynamic radius of the polymer obtained in an aqueous solution, determined by dynamic light scattering, was 440 nm.

EXAMPLE OF PREPARATION B

Into a 5-liter round bottom flask fitted with a stirrer, a reflux condenser, a thermometer and a conduit device for nitrogen and for aqueous ammonia were introduced 2006.2 g of tert-butanol and then 340.0 g of 2-acrylamido-2-methylpropanesulphonic acid, which was dispersed in the solution with energetic stirring. After 30 minutes aqueous ammonia was added via the upper conduit of the round bottom flask and the reaction mixture was kept for 30 minutes at ambient temperature until a pH of the order of 6–6.5 was obtained. 19.2 g of a solution of trimethylolpropane triacrylate at a concentration of 25% in tert-butanol were introduced next and heating to 60° C. was applied while the reaction mixture was simultaneously made inert by introduction of nitrogen into the flask. Once this temperature was reached, dilauroyl peroxide was added. The reaction commenced immediately, which was reflected in a rise in temperature and a precipitation of the polymerizate. 15 minutes after the polymerization began a stream of nitrogen was introduced. 30 minutes after the addition of the initiator the temperature of the reaction mixture reached a maximum of 65–70° C. 30 minutes after having reached this temperature the mixture was heated to reflux and kept in these conditions for 2 hours. A thick paste was seen to form during the reaction.

The product obtained was cooled to ambient temperature and filtered. The paste recovered was next dried under vacuum at 60–70° C. for 24 hours. 391 g of crosslinked and neutralized poly(2-acrylamido-2-methylpropanesulphonic acid) were obtained, which have a viscosity, measured with a Brookfield viscometer, spindle 4, at a speed of rotation of 100 revolutions/minute in a water solution at a concentration of 2% and at 25° C., of the order of 7000 cP.

The hydrodynamic radius of the polymer obtained in an aqueous solution, determined by dynamic light scattering, was 160 nm.

Example 1

| | |
|---|---|
| Phase A | |
| -Octyl palmitate | 5% by weight |
| -Cyclodimethylsiloxane | 5% by weight |
| -Hydrogenated isoparaffin | 5% by weight |
| -Oxyethylenated behenyl alcohol (9 EO) | 4.5% by weight |
| Phase B | |
| -Glycerine | 3% by weight |
| -Distilled water | 13% by weight |
| -Preserving agent | q.s. |
| Phase C | |
| -Distilled water | 50% by weight |
| Phase D | |
| Crosslinked poly(2-acrylamido-2-methylpropanesulphonic acid) neutralized with aqueous ammonia, prepared according to the process of Example of preparation A, with a viscosity of the order of 16000 cP in a water solution at a concentration of 2% and at 25° C. | 0.2–0.5–1% by weight |

Depending on the concentration of the gelling agent (0.2, 0.5 or 1% by weight), more or less translucent and more or less thick formulations were obtained which were stable after 2 months' storage at ambient temperature, at 4° C., at 37° C. and after 1 month at 45° C., and stable after 10 freezing/thawing cycles.

Procedure

Phases A and B were heated to 60° C. and homogenized. Phase B was poured slowly onto phase A with slow stirring and the mixture was heated to the phase inversion temperature (PIT) which is around 80° C. The water-in-oil emulsion obtained became virtually transparent and very bluish. Heating was stopped and phase C was poured while slow stirring was maintained. At ambient temperature an oil-in-water emulsion was obtained by phase inversion, which was next poured onto the phase D and the whole was homogenized with appropriate stirring, using, for example, a Moritz turbine.

Comparative Examples

Three compositions of the invention, 1a, 1b and 1c, were made according to Example 1 defined above, containing 0.2, 0.5 and 1% by weight respectively of crosslinked and more than 90% neutralized poly(2-acrylamido-2-methylpropanesulphonic acid) polymer. Compositions 1a, 1b and 1c were compared with compositions 2a, 2b and 2c and with compositions 3a, 3b and 3c according to the prior art, containing, instead of the poly(2-acrylamido-2-methylpropanesulphonic acid) a conventional gelling agent in the same concentrations as those of inventive compositions 1a, 1b and 1c.

Compositions 2a, 2b, 2c and compositions 3a, 3b and 3c had the following formulation:

Compositions 2a, 2b, 2c: identical with compositions 1a, 1b and 1c according to Example 1 respectively, but containing in phase D 0.2, 0.5 and 1% by weight respectively of a crosslinked and partially or completely neutralized acrylamide/2-acrylamido-2-methylpropanesulphonic acid copolymer in emulsion such as the product SEPIGEL sold by Seppic.

Compositions 3a, 3b and 3c: identical with compositions 1a, 1b, 1c according to Example 1 respectively, but containing in phase D 0.5% by weight of an acrylic acid/sodium acrylate copolymer in emulsion such as the commercial product SALCARE SC 97 sold by the company Allied Colloids.

All these compositions were also compared with a control composition 4, identical with Example 1 and not containing any gelling phase D.

Compositions 1a, 1b, 1c and 2a, 2b, 2c and 3a, 3b, 3c and 4 were prepared according to the procedure described in Example 1. Their final appearance was observed and their stability was studied in storage and after 10 freezing/thawing cycles.

The results of these tests are summarized in the following table:

| COMPOSITIONS | APPEARANCE | STABILITY |
|---|---|---|
| 1a | bluish, very fluid, homogeneous | stable after 2 months at ambient temperature, 4° C., 37° C. stable after 1 month at 45° C. stable after 10 freezing/thawing cycles |
| 1b | slightly bluish, smooth, fairly thick, homogeneous | stable after 2 months at ambient temperature, 4° C., 37° C. and at 45° C. stable after 10 freezing/thawing cycles |
| 1c | fine, white and thick cream, homogeneous | stable after 2 months at ambient temperature, 4° C., 37° C. and at 45° C. stable after 10 freezing/thawing cycles |
| 2a, 2b, 2c | opaque, heterogeneous | a creaming phenomenon is observed a few hours after the manufacture 2 days later the emulsions are heterogeneous |
| 3a, 3b, 3c | opaque, heterogeneous | unstable emulsions separation into two phases |
| 4 | bluish, very fluid, homogeneous | a few days after the manufacture, appearance of a gelled phase deposited at the bottom of the flask |

What is claimed is:

1. A cosmetic or dermatological composition in the form of an ultra-fine oil-in-water emulsion comprising a dispersed fatty phase and a dispersing aqueous phase, wherein said fatty phase comprises particles or globules having a mean size within said dispersing aqueous phase of from 50 nm to 1000 nm, further wherein the composition contains at least one crosslinked poly(2-acrylamido-2-methylpropanesulphonic acid) polymer which comprises, distributed randomly:

(a) from 90 to 99.9% by weight, relative to the weight of said at least one crosslinked polymer, of units of following formula (1):

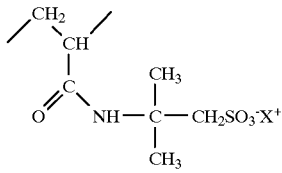

in which $X^+$ denotes a cation or a mixture of cations, it being a possible for at the most 10 mol % of the cations $X^+$ to be protons $H^+$; and (b) from 0.01 to 10% by weight, relative to the weight of said at least one crosslinked polymer, of crosslinking units originating from at least one monomer containing at least two olefinic double bonds, and further wherein said crosslinked poly(2-acrylamido-2-methylpropanesuphonic acid) polymer is neutralized to at least 90%.

2. A composition according to claim 1, wherein said composition is obtained according to an emulsifying technique using phase inversion.

3. A composition according to claim 1, wherein said at least one crosslinked poly(2-acrylamido-2-methylpropanesulphonic acid) polymer comprise a number of units of formula (1) in a quantity which is sufficiently high to obtain polymer particles whose hydrodynamic volume in solution in water has a radius ranging from 10 to 500 nm and whose distribution is homogeneous and unimodal.

4. A composition according to claim 1, wherein said at least one crosslinked poly(2-acrylamido-2-methylpropanesulphonic acid) polymer comprises from 98 to 99.5% by weight of units of formula (1) and from 0.2 to 2% by weight of crosslinking units.

5. A composition according to claim 1, wherein in formula (1) the cation $X^+$ is $NH_4^+$.

6. A composition according to claim 1, wherein said crosslinking units originating from at least one monomer correspond to the following formula (2):

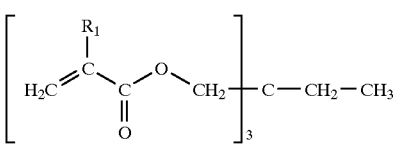

in which $R_1$ denotes hydrogen or a $C_1$–$C_4$ alkyl.

7. A composition according to claim 1, wherein the poly(2-acrylamido-2-methylpropanesulphonic acid) is crosslinked with trimethylolpropane triacrylate.

8. A composition according to claim 1, wherein the polymers of formula (1) exhibit a viscosity, measured with a Brookfield viscometer, spindle 4, speed 100 revolutions/minute, in a water solution at a concentration of 2% and at 25° C., which is higher than or equal to 1000 cP.

9. A composition according to claim 8, wherein the polymers of formula (1) exhibit a viscosity ranging from 5000 to 40,000 cP.

10. A composition according to claim 9, wherein the polymers of formula (1) exhibit a viscosity ranging from 6500 to 35,000 cP.

11. A composition according to claim 1, wherein said at least one crosslinked poly(2-acrylamido-2-methylpropanesulphonic acid) polymer is present in concentrations ranging from 0.1 to 10% by weight relative to the total weight of the composition.

12. A composition according to claim 11, wherein said at least one crosslinked poly(2-acrylamido-2-methylpropanesulphonic acid) polymer is present in concentrations ranging from 0.1 to 0.5% by weight relative to the total weight of the composition.

13. A composition according to claim 1, wherein the mean size of said liquid particles or globules of said fatty phase within the dispersing aqueous phase ranges from 70 nm to 350 nm.

14. A composition according to claim 13, wherein the mean size of said liquid particles or globules of said fatty phase within the dispersing aqueous phase ranges from 70 nm to 300 nm.

15. A composition according to claim 1, wherein 90% of the particles of said oil-in-water emulsion have a size ranging from 100 nm to 300 nm and further wherein the difference in size between the largest and the smallest particles is from 20 to 400 nm.

16. A composition according to claim 15, wherein the difference in size between the largest and the smallest particles ranges from 30 to 200 nm.

17. A composition according to claim 1, wherein said dispersing aqueous phase is water, a mixture of water and at least one polyhydric alcohol or a mixture of water and at least one water-soluble lower alcohol.

18. A composition according to claim 1, wherein said dispersing aqueous phase represents from 50 to 95% by weight of the total quantity of the composition.

19. A composition according to claim 18, wherein said dispersing aqueous phase represents from 70 to 90% by weight of the total quantity of the composition.

20. A composition according to claim 1, wherein said dispersed fatty phase comprises at least one compound usually employed in oil-in-water emulsion, said at least one compound being selected from fatty substances, oils of vegetable, animal, synthetic or mineral origin, natural or synthetic waxes, and mixtures thereof.

21. A composition according to claim 1, wherein said dispersed fatty phase represents from 0.5 to 50% by weight of the total quantity of the composition.

22. A composition according to claim 21, wherein said dispersed fatty phase represents from 10 to 30% by weight of the total quantity of the composition.

23. A composition according to claim 1, wherein said composition contains at least one emulsifying agent selected from nonionic compounds containing at least one lipophilic residue and at least one hydrophilic residue.

24. A composition according to claim 23, wherein said at least one lipophilic residue is a $C_6$–$C_{30}$ alkyl or acyl functional group.

25. A composition according to claim 23, wherein said at least one hydrophilic residue is a glycol group, a glucose or a polyol ether.

26. A composition according to claim 23, A wherein said at least one emulsifying agent has an HLB ranging from 9 to 18.

27. A composition according to claim 23, wherein said at least one emulsifying agent is selected from the product of addition of (a) ethylene oxide to fatty alcohols containing 6 to 30 carbon atoms or to partial esters of polyols containing 3 to 16 carbon atoms and of (b) fatty acids containing 14 to 22 carbon atoms.

28. A composition according to claim 27, wherein said at least one emulsifying agent is (a) a compound corresponding to the formula (IV):

$$R^4-(O-CH_2-CH_2)_n-OH \quad (IV)$$

in which $R^4$ denotes a branched or linear, saturated or unsaturated hydrocarbon residue containing from 8 to 28 carbon atoms and n denotes a number ranging from 8 to 50; or (b) a product of addition of 4 to 20 moles of ethylene oxide to one or several partial esters of glycerol.

29. A composition according to claim 28, wherein, in said compound corresponding to the formula (IV), n denotes a number ranging from 8 to 30.

30. A composition according to claim 23, wherein said at least one emulsifying agent is present in an amount ranging from 0.5 to 30% by weight relative to the total weight of the composition.

31. A composition according to claim 30, wherein said at least one emulsifying agent is present in an amount ranging from 2 to 10% by weight relative to the total weight of the composition.

32. A composition according to claim 23, wherein said composition additionally contains at least one coemulsifying agent selected from $C_{16}$–$C_{22}$ fatty alcohols and the partial esters of $C_3$–$C_6$ polyols with $C_{14}$–$C_{22}$ fatty acids.

33. A composition according to claim 32, wherein said composition contains said at least one emulsifying agent and said at least one coemulsifying agent in a combined amount from 0.5 to 30% by weight relative to the total weight of the composition.

34. A composition according to claim 31, wherein said composition contains said at least one emulsifying agent and said at least one coemulsifying agent in a combined amount ranging from 2 to 10% by weight relative to the total weight of the composition.

35. A composition according to claim 1, wherein said composition additionally contains at least one additive selected from aqueous or lipophilic conventional gelling agents or thickeners, hydrophilic or lipophilic active substances, preserving agents, antioxidants, perfumes, hydrating agents, emollients, sequestrants, surfactants, polymers, alkalifying or acidifying agents, fillers, agents against free radicals, ceramides, sunscreens, insect repellents, slimming agents, coloring agents, bactericides and agents against dandruff.

36. A process for nontherapeutic cosmetic treatment of the skin, hair, scalp, eyelashes, eyebrows, nails or mucosae, said process comprising applying a composition according to claim 1 to said skin, hair, scalp, eyelashes, eyebrows, nails or mucosae.

37. A process according to claim 36, wherein said composition is a hair-care product, a make-up product or an antisun product.

38. A process for the preparation of a composition according to claim 1, wherein the composition is obtained by:
    (1) mixing
        (a) at least one cosmetic oil,
        (b) at least one emulsifier and optionally a coemulsifier,
        (c) water, and optionally
        (d) adjuvants which are stable at the phase inversion temperature,
    to obtain a conventional emulsion;
    (2) heating said emulsion wherein said emulsion is either heated to a temperature situated within or above the phase inversion region or preparing said emulsion at a temperature situated within or above the phase inversion region;
    (3) cooling said emulsion to a temperature lower than the phase inversion region; and
    (4) gelling said emulsion by adding at least one crosslinked poly(2-acrylamido-2- methylpropanesulphonic acid) polymer as defined in claim 1 as a gelling agent.

39. A process for the therapeutic treatment of the face, hands or human body, wherein a composition according to claim 1 is applied to said face, hands or human body.

40. A process according to claim 39, wherein said composition is a salve or an ointment.

41. A process for gelling or thickening a cosmetic or dermatological composition in the form of an ultrafine oil-in-water emulsion comprising an aqueous phase and a fatty phase, wherein said fatty phase comprises globules having a mean size of from 50 nm to 1000 nm, said process comprising adding at least one crosslinked poly(2-acrylamido-2-methylpropanesulphonic acid) polymer as defined in claim 1 to said cosmetic or dermatological composition as a gelling agent or thickening agent.

42. A process for stabilizing a cosmetic or dermatological composition in the form of ultrafine oil-in-water emulsion comprising an aqueous phase and a fatty phase, wherein said fatty phase comprises globules having a mean size of from 50 nm to 1000 nm, said process comprising adding at least one crosslinked poly(2-acrylamido-2-methylpropanesulphonic acid) polymer as defined in claim 1 to said cosmetic or dermatological composition as a stabilizer.

\* \* \* \* \*

UNITED STATES PATENT AND TRADEMARK OFFICE
CERTIFICATE OF CORRECTION

PATENT NO.: 5,952,395

DATED: September 14, 1999

INVENTOR(S): LORANT

It is certified that errors appear in the above-identified patent and that said Letters Patent is hereby corrected as shown below:

In claim 1, column 12, line 12, delete the word "a".

In claim 26, column 13, line 56, before "wherein," delete the word "A".

Title page, item [54], line 6 of Title, "90% PROCESS" should read --90%, PROCESS--.

Signed and Sealed this

Twenty-fifth Day of April, 2000

Attest:

Attesting Officer

Q. TODD DICKINSON

Director of Patents and Trademarks